US008939949B2

(12) United States Patent
Bourne (10) Patent No.: US 8,939,949 B2
(45) Date of Patent: Jan. 27, 2015

(54) STACKED MULTI-DISK OPHTHALMIC PUMP

(75) Inventor: John M. Bourne, Tustin, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 384 days.

(21) Appl. No.: 13/209,734

(22) Filed: Aug. 15, 2011

(65) Prior Publication Data

US 2013/0046228 A1 Feb. 21, 2013

(51) Int. Cl.
*A61M 1/00* (2006.01)
*A61F 9/007* (2006.01)

(52) U.S. Cl.
CPC .......... *A61F 9/00736* (2013.01); *A61M 1/0039* (2013.01)
USPC ............................. 604/315; 415/90; 417/423.1

(58) Field of Classification Search
USPC ............. 604/131, 315; 415/90; 416/4, 198 R; 417/321, 410.1, 423.1, 424.1, 424.2
See application file for complete search history.

(56) References Cited

U.S. PATENT DOCUMENTS

| 1,061,142 | A | 5/1913 | Tesla |
| 1,061,206 | A | 5/1913 | Tesla |
| 3,487,784 | A * | 1/1970 | Rafferty et al. ............... 415/119 |
| 4,255,081 | A | 3/1981 | Oklejas et al. |
| 4,921,477 | A | 5/1990 | Davis |
| 5,046,486 | A * | 9/1991 | Grulke et al. ................. 601/161 |
| 6,599,277 | B2 | 7/2003 | Neubert |
| 7,393,189 | B2 | 7/2008 | Davis et al. |
| 7,695,242 | B2 | 4/2010 | Fuller |
| 2006/0253194 | A1 | 11/2006 | Dial |
| 2007/0135760 | A1 | 6/2007 | Williams |
| 2009/0317271 | A1 | 12/2009 | Gill et al. |
| 2011/0137231 | A1 | 6/2011 | Sorensen et al. |
| 2011/0144567 | A1 | 6/2011 | Sorensen et al. |

OTHER PUBLICATIONS

Sorensen, Gary, Phacoemulsification Hand Piece with Integrated Aspiration Pump, U.S. Appl. No. 13/325,549, filed Dec. 14, 2011, 18 pages.
http://www.advancedfluid.com/discflo/concepts.htm, web archive dated Aug. 8, 2008, 3 pages.

* cited by examiner

*Primary Examiner* — Kami A Bosworth
(74) *Attorney, Agent, or Firm* — Haynes and Boone, LLP (57) ABSTRACT

The present disclosure relates to a stacked multi-disk pump for the pumping of ocular fluid and/or tissue during ophthalmic surgery. The stacked multi-disk pump includes an inlet port, a stacked multi-disk assembly, a fluid chamber, a central hub, a motor, and an outlet port. The motor and the hub induce the multi-disk assembly to rotate. As the multi-disk assembly rotates, the fluid is propelled into the inlet port, progresses axially, circumferentially, and radially through the stacked multi-disk assembly, and flows out the outlet port. The pump may be incorporated, for example, into the handpiece of an ophthalmic surgical instrument or a surgical console.

22 Claims, 4 Drawing Sheets

STACKED MULTI-DISK OPHTHALMIC PUMP

BACKGROUND

During ophthalmological surgeries, various volumetric and vacuum pumps have been used to remove fluid and other material from the surgical site. For example, in ophthalmic surgical systems, a peristaltic pump may be used to regulate the flow of fluid from and to the surgical site during vitrectomies, cataract removals, and other ophthalmic procedures. Such peristaltic pumps have the disadvantages of introducing a pulsatile flow effect to the aspiration procedure and requiring a consumable intermediary attachment for aspiration pumping. Also, because the pump acts directly on the intermediary consumable attachment, instead of on the fluid to be displaced, the power requirements and necessary motor size are increased. In addition, peristaltic pumps do not allow for the most efficient displacement of viscous fluid or fluid containing debris and other material.

Alternatively, vacuum pumps placed in surgical consoles located a distance away from the patient, such as Venturi pumps or rotary vane pumps (bladed centrifugal pumps), may be utilized. However, rotary vane pumps have various deficiencies that limit the usefulness of such pumps in ophthalmic applications. Pumps employing vanes, paddles, blades, etc. operate by colliding with and physically redirecting the fluid being displaced. This method of operation introduces vibrations and turbulence to the fluid, which impedes the movement of the fluid and the overall efficiency of the system. In addition, rotary vane pumps can have cavitation problems, low efficiency when pumping viscous fluids, and a low resistance to wear when pumping abrasive fluids.

A need exists for a pump designed for use in ophthalmic surgeries that displaces fluids in such a manner as to allow movement along the path of least resistance, thereby reducing pulsatile flow, turbulence, and cavitation in the fluid, increasing pumping efficiency, and increasing pump resistance to wear.

SUMMARY

This disclosure relates generally to, and encompasses, an apparatus and method for pumping fluid from the eye, and more specifically to a stacked multi-disk pump for the pumping of ocular fluid and/or tissue during ophthalmic surgery.

In one exemplary embodiment, an ophthalmic surgical instrument for pumping fluid from the eye of a patient comprises a cannulated probe and a pump. The pump may comprise a housing, a disk assembly, and a motor. The housing may include a fluid chamber, an inlet port coupled to the probe, and an outlet port. The disk assembly may be located within the fluid chamber and may comprise a stacked array of spaced apart parallel disks. Each of the disks may include a central aperture, wherein the disks are aligned and fixedly spaced from each other along a longitudinal axis extending through the central apertures. The motor may be connected to the disk assembly and configured to rotate the disk assembly to convey fluid into the inlet port, through the central apertures, between the spaced apart disks, and through the outlet port.

In another exemplary embodiment, an ophthalmic surgical instrument for pumping fluid from an eye of a patient comprises a probe sized for insertion into the fluid in the eye and a pump. The pump may comprise a housing, a hub, a motor, a drive shaft, and a disk assembly. The housing may include a fluid chamber, a motor housing chamber, an inlet port, and an outlet port. The hub may be located within the motor housing chamber. The motor may be located within the motor housing chamber and connected to the hub such that the motor is configured to power the rotation of the hub. The drive shaft may comprise an elongate, rigid rod connected to the hub such that rotation of the hub causes rotation of the drive shaft. The drive shaft may extend through the fluid chamber along the longitudinal axis of the pump. The disk assembly may be attached to the drive shaft and comprise a stack of parallel, circular disks. Each disk may extend radially and concentrically from the drive shaft and be spaced axially apart from adjacent disks to form a plurality of fluid flow passages. Each of the disks may include a central aperture in fluid communication with the fluid flow passages, wherein the drive shaft extends through the central apertures. Rotation of the drive shaft may cause rotation of the disk assembly to convey the fluid into the inlet port, through the central apertures and the fluid flow passages of the disk assembly, and through the outlet port.

In another exemplary embodiment, a method of pumping ocular material from an eye comprises providing a surgical instrument, which may comprise a probe and a pump, inserting the probe into a portion of the eye that includes the ocular material, activating the motor to rotate the stacked multi-disk assembly, and conveying the ocular material from the probe through the inlet port, through the fluid flow passages of the disk assembly, and through the outlet port. The pump may comprise a motor, an inlet port, an outlet port, and a multi-disk assembly including a stacked array of alternating disks and fluid flow passages.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION OF THE PREFERRED EMBODIMENTS

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to a system and method for pumping biological fluid. More particularly, but not be way of limitation, the present disclosure pertains to a stacked multi-disk pump for the pumping of ocular fluid and/or tissue during ophthalmic surgery.

The various figures show embodiments of an ophthalmic surgical instrument and methods of using the device to remove ocular fluid and/or tissue from a patient's eye. One of ordinary skill in the art, however, would understand that similar embodiments could be used to remove fluid and/or tissue from other locations in the body without departing from the general intent or teachings of the present disclosure.

Figure 1:
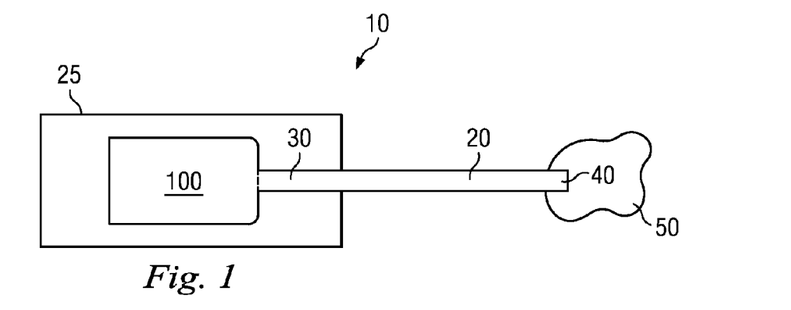
FIG. 1 is a schematic drawing representing an ophthalmic instrument according to an embodiment of the present disclosure.

FIG. 1 is a schematic drawing representing an ophthalmic surgical instrument 10 according to an embodiment of the present disclosure. The ophthalmic instrument 10 includes a probe 20 extending from a handpiece 25. A stacked multi-disk pump 100 is housed within the handpiece 25. The stacked multi-disk pump 100 will be described in greater detail in association with FIG. 2. The probe 20 may be integrally connected to the handpiece 25 or may be a separate, detachable component of the instrument 10. The probe 20 extends from the handpiece 25 and includes a proximal end 30 and a distal end 40. The proximal end 30 is in fluid communication with the stacked multi-disk pump 100. The distal end 40 is in fluid communication with a fluid source 50, such as a surgical site within the eye of a patient. The ophthalmic instrument 10 utilizes the stacked multi-disk pump 100 to aspirate fluid from the fluid source 50 through the probe 20, through the pump 100, and into an optional collection site. In other embodiments, the ophthalmic instrument 10 utilizes the stacked multi-disk pump 100 to pump fluid from the pump 100 into the probe 20. The ophthalmic instrument 10 can be any of a variety of surgical ophthalmic instruments, including, a vitrectomy probe or a Phaco handpiece combination, for example. It is contemplated that other embodiments may include a remotely-positioned console to house the pump 100, instead of or in addition to the handpiece 25.

Figure 2:
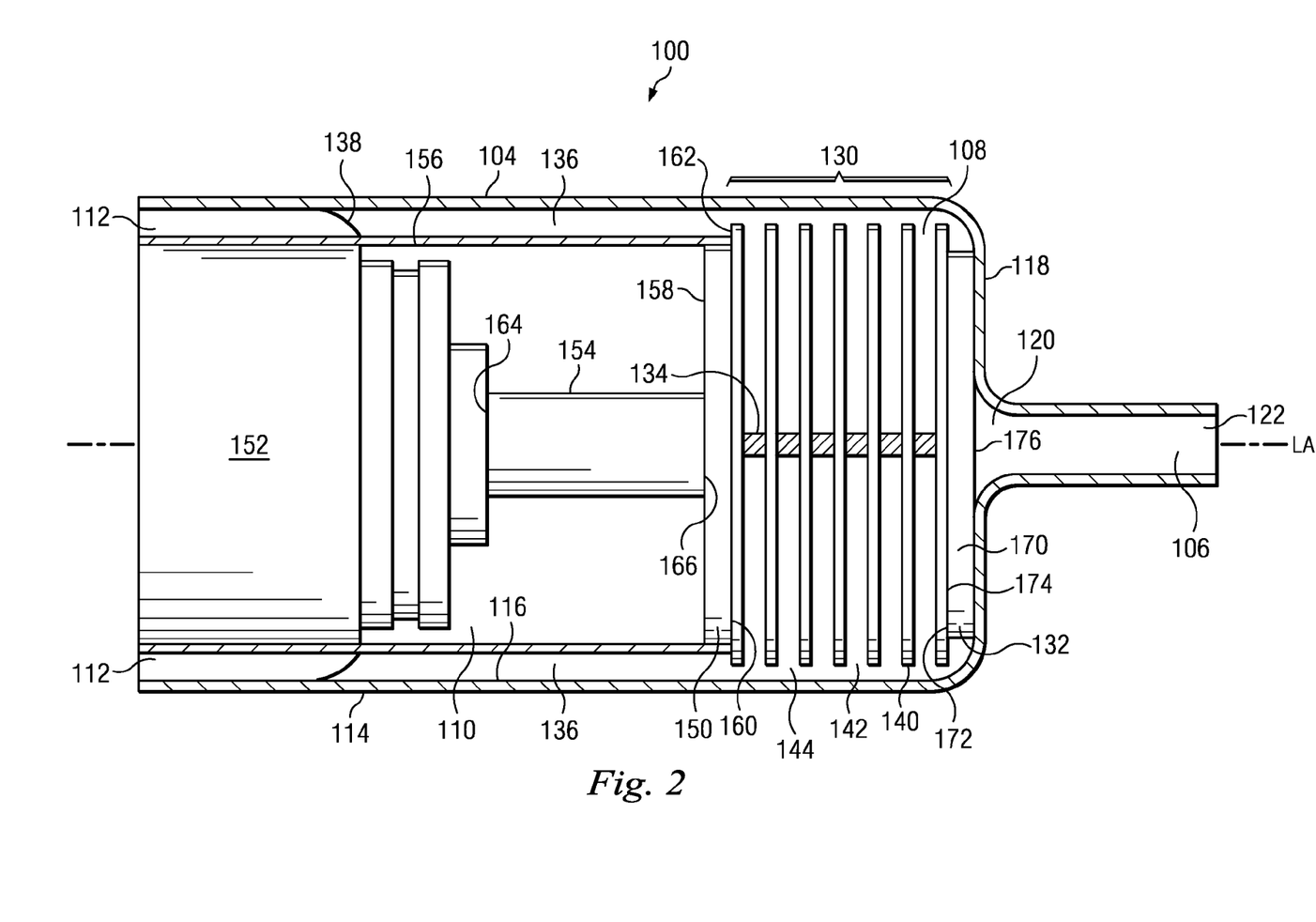
FIG. 2 is a cross-sectional side view of a portion of an ophthalmic instrument including a stacked multi-disk pump according to an embodiment of the present disclosure.

FIG. 2 illustrates a stacked multi-disk pump 100 according to an exemplary embodiment of the present disclosure for removing fluid/tissue from a patient's eye. The stacked multi-disk pump 100 includes a generally cylindrical housing 104 having a longitudinal axis LA. In some embodiments, the longitudinal axis LA of the pump 100 is aligned with the longitudinal axis of the instrument 10. The housing 104 comprises an inlet port 106, a fluid chamber 108, a motor housing chamber 110 and an outlet port 112. The housing 104 comprises an outer wall 114 and an inner wall 116. The outer wall 114 includes a distal face 118. The inlet port 106 includes two ends, a proximal end 120 and a distal end 122. The fluid chamber 108 houses a disk assembly 130, a distal plate 132, a drive shaft 134, an outflow passage 136, and an outflow valve 138. The disk assembly 130 includes individual disks 140 arranged in a cylindrical stack with distinct fluid flow passages 142 between each disk 140. A space 144 exists between the disk assembly 130 and the inner wall 116 of the housing 104. The motor housing chamber 110 houses a proximal plate 150, a motor 152, and a hub 154. The motor housing chamber 110 is defined by the motor housing wall 156, which separates the motor housing chamber 110 from the fluid chamber 108. In other embodiments, the pump 100 may lack a distal plate 132, a drive shaft 134, and/or an outflow valve 138.

The housing 104 may be of any conventional design that provides a complementary surface for the internal components of the pump 100. In FIG. 2, the housing 104 is generally configured as a hollow cylinder. The housing 100 forms a cavity large enough to contain both the fluid chamber 108 and the motor housing chamber 110. Other embodiments may utilize any conventional housing that accommodates the internal components of the pump 100, and are not limited to the exemplary embodiment presented in FIG. 2.

The inlet port 106 is shaped and configured to receive fluid into the pump 100. In FIG. 2, the inlet port 106 comprises a cylindrical tube centrally located on the distal face 118 of the housing 104. The inlet port 106 is shown extending from the face 118 of the housing 104 in substantial alignment with the longitudinal axis LA of the pump 100. The inlet port 106 includes two ends, a proximal end 120 and a distal end 122. The proximal end 120 is in fluid communication with the fluid chamber 108. The inlet port 106 allows fluid to enter the fluid chamber 108 through the proximal end 120 along an axis that is substantially parallel to the longitudinal axis LA. The distal end 122 is in fluid communication with the fluid to be displaced from the surgical site. For example, the distal end 122 of the inlet port 106 may be in fluid communication with a surgical probe 20 that is in contact with fluid (as illustrated in FIG. 1). In some embodiments, the distal end 122 of the inlet port 106 may interconnect with the proximal end 30 of the probe 20 by any of a variety of known connection mechanisms, including threaded, biased, or snap-fit mechanisms, for example. The inlet port 106 may interconnect with the probe 20 either inside or outside the handpiece 25. In other embodiments, the distal end 122 of the inlet port 106 may directly contact aqueous humor or vitreous humor within the eye of a patient. The inlet port 106 may comprise any of a variety of shapes, sizes, and configurations provided the inlet port 106 permits the inflow of fluid into the pump 100. In some embodiments, the inlet port 106 is rigid. In other embodiments, the inlet port 106 is semi-rigid with varying degrees of flexibility.

The fluid chamber 108 is at least partially defined by the inner wall 116 of the housing 104 and the wall 156 of the motor housing chamber 110. The fluid chamber 108 isolates the fluid from the motor housing chamber 110 as the fluid travels through the pump 100. The fluid chamber 108 is sized and configured to accommodate the disk assembly 130 while maintaining a uniform space 144 between the disk assembly 130 and the inner wall 116 of the housing 104. In other embodiments, the space 144 is not uniformly disposed around the disk assembly 130.

As will be explained in further detail below, the inner wall 116 of the housing 104 provides a complementary surface for the fluid outflow of the disk assembly 130. The space 144 permits movement of the fluid around the disk assembly 130 within the fluid chamber 108 and creates a cylindrical zone of high pressure. The volume defined by the space 144 impacts the flow rate and the operating pressure of the pump 100. Various factors to be considered in determining the volume of the space 144 include, but are not limited to, the volume of the inlet port 106, the output pressure at the outlet ports 112, and the viscosity of the fluid. In some embodiments, the inner wall 116 of the housing 104 is shaped to provide an accessory fluid channel by an inwardly angled shelf or groove in the wall 116 adjacent to the disk assembly 130.

The disk assembly 130 comprises the plurality of disks 140 longitudinally aligned in a cylindrical stack with distinct fluid flow passages 142 between each disk 140. Each disk 140 is stacked axially apart and parallel to the adjacent disk 150 to define the toroid-shaped gaps, or fluid flow passages 142, extending therebetween. Each of the disks 140 forming the disk assembly 130 preferably has the same shape, diameter, and configuration, and is aligned parallel to the adjacent disk 140 in a consistent fashion to form a cylindrical stack along the longitudinal axis LA of the pump 100. The disks 140 and the disk assembly 130 will be described in further detail in association with FIGS. 3 and 4, respectively.

The disk assembly 130 is rotatably mounted in the fluid chamber 108. In the embodiment shown in FIG. 2, the disk assembly 130 is mounted around the drive shaft 134 such that the disk assembly 130 and the inlet port 106 are substantially aligned. As will be described further below, fluid enters the disk assembly 130 through the inlet port 106 and exits the disk assembly 130 into the space 144. The fluid outflow from the disk assembly 130 travels through the space 144 toward the outflow passage 136.

In the embodiment pictured in FIG. 2, the outflow passage 136 comprises an annular space or passageway disposed circumferentially around the motor housing chamber 110 and extending to the outlet port 112, which comprises an annular port disposed around the motor housing chamber 110. In other embodiments, the inner wall 116 of the housing 110 may be configured such that the space 144 is not uniformly disposed around the disk assembly 130, the outflow passage 136 comprises a tube disposed along one side of the motor housing or the disk assembly 130, and/or the space 144 is configured to direct the fluid into the outflow passage 136 and through the outflow valve 138. The outflow valve 138 may comprise any of a variety of known one-way flow valves that prevent fluid from re-entering the fluid chamber 108.

As shown in FIG. 2, the pump 100 further comprises a motor housing chamber 110 housing a motor 152, a hub 154, and a proximal plate 150. The motor 152 may be any type of drive system capable of indirectly or directly imparting rotational movement to the hub 154, thereby imparting rotational movement to the disk assembly 130. Suitable drive systems include motors of all types, including magnetic drive systems.

The hub 154 is a cylindrical, substantially rigid rod disposed within the motor housing chamber 110 and substantially co-aligned with the disk assembly 130. The hub 154 includes a proximal side 164 and a distal side 166. The proximal side 164 of the hub 154 is either integrally formed with the motor 152 or attached to the motor 152 via any one of a variety of connection mechanisms, including adhesive, welding, or mechanical joints. For example, the proximal side 164 of the hub 154 may be keyed with a receiving notch for receiving a complementary retaining device disposed on the motor 152. Regardless of the method of connection to the motor 152, the hub 154 indirectly couples the motor 152 to the disk assembly 130.

The proximal plate 150 is a flat, substantially rigid, solid, cylindrical disk having a proximal face 158 and a distal face 160. The proximal face 158 of the proximal plate 150 contacts the hub 154 to fixedly couple the proximal plate 150 to the hub 154. In FIG. 2, the distal face 160 contacts the proximal face of the most proximal disk 162. In some embodiments, the distal face 160 of the proximal plate 150 is fixedly coupled to the proximal face of the most proximal disk 162. In other embodiments, the proximal plate 150 may be spaced apart from and not directly coupled to the most proximal disk 162. In some embodiments, the proximal plate is fixedly and centrally coupled to the drive shaft 134 through a central aperture or indentation.

In the pictured embodiment, the hub 154 couples the motor 152 to the disk assembly 130 via the drive shaft 134 and the proximal plate 150. The distal side 166 of the hub 154 is fixedly coupled to the drive shaft 134 and the proximal plate 150. In alternative embodiments, the hub 154, the drive shaft 134, and/or the proximal plate 150 may be one integrally-formed component. The drive shaft 134 and/or the proximal plate 150 may be integrally formed with the hub 154, or attached to the hub 154 using a variety of known methods, such as adhesive bonding, lamination between two layers of polymers, or welding, for example.

The drive shaft 134 is a rigid, elongate, cylindrical rod extending perpendicularly from the distal side 166 of the hub 154 along the longitudinal axis LA. The drive shaft 134 extends longitudinally through the center of the disk assembly 130. The drive shaft 134 is coupled to the hub 154 such that the drive shaft 134 co-rotates in unison with the hub 154. In the embodiment shown in FIG. 2, the disk assembly 130 is attached to the drive shaft 134 and therefore co-rotates in unison with the drive shaft 134 (and therefore the hub 154). If the hub 154 is not in motion, the drive shaft 134 and the disk assembly 130 are also not in motion. If the hub 154 rotates, the drive shaft 134 exhibits an identical and simultaneous rotation, thereby rotating the disk assembly 130 in unison with the rotation of the hub 154.

As shown in FIG. 2, a distal plate 170 is disposed adjacent the most distal disk 172 in the fluid chamber 108. The distal plate 170 is a flat, substantially rigid, cylindrical disk having a proximal face 174, a distal face 176, and a central aperture 178 (shown in FIG. 5). The proximal face 174 of the distal plate 170 contacts the most distal disk 172. In FIG. 2, the distal face 172 of the distal plate 170 contacts the inner wall 116 of the housing 104. In some embodiments, the proximal face 160 of the distal plate 170 is fixedly coupled to the distal face of the most distal disk 172 such that the distal plate 170 rotates in unison with the rotation of the disk assembly 130. In other embodiments, the distal plate 170 may be spaced apart from and not directly coupled to the most distal disk 172. In some embodiments, the distal plate 170 is fixedly and centrally coupled to the drive shaft 134 such that the distal plate rotates in unison with the rotation of the drive shaft 134. Fluid flows from the inlet port 106 through the central aperture 178 of the distal plate 170 into the disk assembly 130. In some embodiments, the pump 100 lacks a distal plate 170. In some embodiments, a cap is mounted on the distal face 176 of the distal plate 170 to secure the distal plate 170 in a fixed axial position relative to the disk assembly 130.

In the pictured embodiment, the proximal plate 150 and the distal plate 170 are thicker than the disks 140, thereby providing additional mechanical support to the disk assembly 130 to counteract any negative pressure created in the fluid flow passages 142, particularly at the outer periphery of the disks 140. The plates 150, 170 reinforce and support the disks 140 by providing a solid and relatively inflexible surface for the disks 140 to pull against, thereby reducing the tendency of the disks 140 to inwardly deflect in response to the negative pressure. In other embodiments, the proximal plate 150 and/or the distal plate 170 may have the same or lesser thickness than a disk 140.

Figure 3:
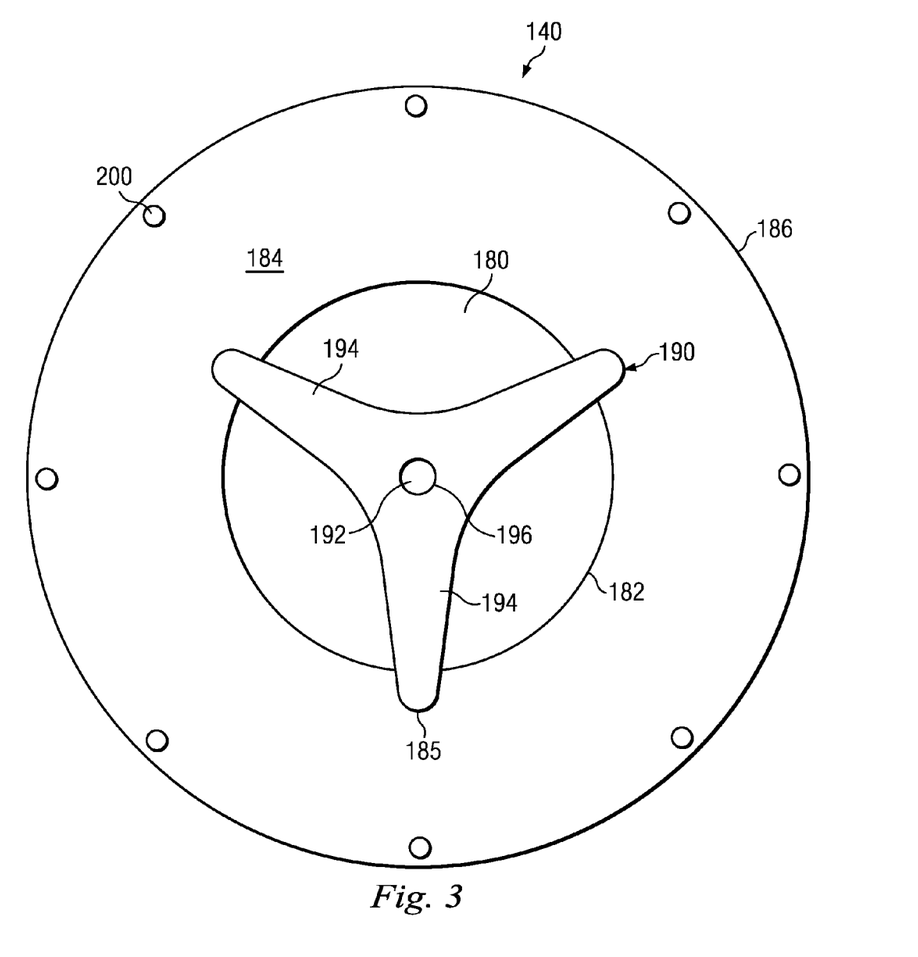
FIG. 3 is a plan view of a single disk of a stacked multi-disk pump within an ophthalmic instrument according to an embodiment of the present disclosure.

As shown in FIG. 3, each disk 140 is shaped and configured to be substantially flat and circular with a central aperture 180, which defines an inner perimeter 182 of each disk 140. The face 184 of the disk 140 faces the inlet port 106 and forms the viscous drag surface area of the disk 140. The face 184 defines the outer perimeter 186 of each disk 140. The face 184 is substantially flat and devoid of any purposefully raised elements, such as protrusions, engravings, and/or grooves. However, alternative embodiments may have textured faces 184 such that the face 184 provides a roughened surface supplying additional friction for displacing fluid. Some embodiments may include attachment features 185 inset along or in close proximity to the inner perimeter 182 of the disks 140. In alternative embodiments, the attachment features 185 may protrude into the central aperture 180. As described below, the attachment features 185 serve to support an alternating stack of disks 140 and fluid flow passages 142 to form a disk assembly 130. The number, position, and configuration of attachment features 185 vary depending upon the specific application of the pump 100.

The dimensions and materials of the disks 140 are dependent upon the specific application involved, in particular the viscosity of the fluid, the desired flow rate, and the resultant operating pressures. In the embodiments pictured herein, each disk 140 is sized and shaped identically. However, each disk 140 need not be sized identically. In general, the dimensions of each disk 140, such as overall diameter and central aperture diameter, are variable and determined by the particular use of the pump 100. The number and size of disks 140 in the disk assembly 130 is also influenced by the size of the housing 104 and the desired flow rate of a particular fluid. For example, disks may range from 0.375 inches to 2 inches in outer diameter in a handpiece application, and may range from 2 inches to 10 inches in outer diameter in a console application. Because the viscous drag surface areas of the faces 184 significantly affect the flow of fluid, it may be desirable that the disks 140 be as thin as possible for any given application. Therefore, it may be preferable that the disks 140 have a thickness capable of maintaining sufficient mechanical strength and rigidity against the stresses encountered by the pump 100, yet are as thin as possible to reduce unnecessary turbulence and cavitation. In one embodiment, it is desirable to make the disks 140 as thin as possible, while maintaining the desired structural integrity for pumping biocompatible fluids. Thinner disks allow for greater total surface area of the disk assembly 130 at the cost of reducing the strength of the disks and increasing the risk of breakage, bending, or vibration. For example, disks may range from 0.005 inches to 0.063 inches in thickness, depending upon the specific application of the pump 100. The central aperture 180 may range from 0.06 inches to 1.5 inches in diameter, depending upon the specific application of the pump 100.

The disks 140 may be constructed of any suitable material possessing sufficient mechanical strength, rigidity, and durability to function in the pump 100, as well as physical and chemical inertness to the fluid being displaced. For example, in an exemplary embodiment, the disk material would be resistant to extreme temperatures and pH and biocompatible with ophthalmic fluids and/or tissue and/or medications. The disks 140 may, by way of example but not by way of limitation, be composed of metal, metal alloys, ceramics, or rigid plastics.

FIG. 3 illustrates a central spacer 190 (not shown in FIG. 1) disposed within the central aperture 180 of the disk 140. The central spacers 190 maintain the spaces between the disks 140, or the height of the fluid flow passages 142. In the embodiment illustrated in FIG. 3, the central spacers 190 are shaped and configured as substantially flat, Y-shaped components having a central opening 192 and prongs 194. The central spacers 190 may comprise any of a variety of suitable shapes that do not create undue turbulence in the fluid medium, such as, but not by way of limitation, round, oval, polygonal, oblong, and the like. The spacers 190 may have any number of prongs 194. The spacers 190 may have uniform or non-uniform areas throughout their cross-section and their profile may present straight or curved lines. In some embodiments, the central openings 192 are sized and shaped to slidably accommodate the drive shaft 134, and the central spacers 190 are attached to the drive shaft 134 along the inner perimeter 196 of the central openings 192 by any of a variety of known methods, including, adhesive, welding, or mechanical connectors, for example. In some embodiments, the prongs 194 of the central spacers 190 may be fixedly attached to the adjacent disks 140 (near the inner perimeter 182) by any of a variety of known methods, including, adhesive, welding, or mechanical connectors, for example. Alternative embodiments may have the central spacers 190 integrated into the disks 140 or the attachment features 185. The central spacers 190 may be composed of any suitable material compatible with other components of the pump 100 and the fluid being displaced, such as metals, metal alloys, ceramics, and/or plastics, for example.

As shown in FIG. 3, the disk 140 may also include a plurality of connectors 200 disposed circumferentially near the outer perimeter 186 around the face 184. In the pictured embodiment, the connectors 200 are shaped as raised, circular elements. In other embodiments, the connectors may be shaped and configured in any of a variety of suitable shapes that do not create undue turbulence in the fluid medium or block outward flow, such as elliptical, arcuate, polygonal, parabolic, oblong, tear-drop, and the like, for example. The disk 140 may have any of a number of connectors 200 arranged on the face 184 in any suitable pattern and design. Moreover, the connectors 200 may be of variable lengths relative to the radius of the disk 140, and the connectors 200 may also vary angular position relative to the central aperture 180.

Figure 4:
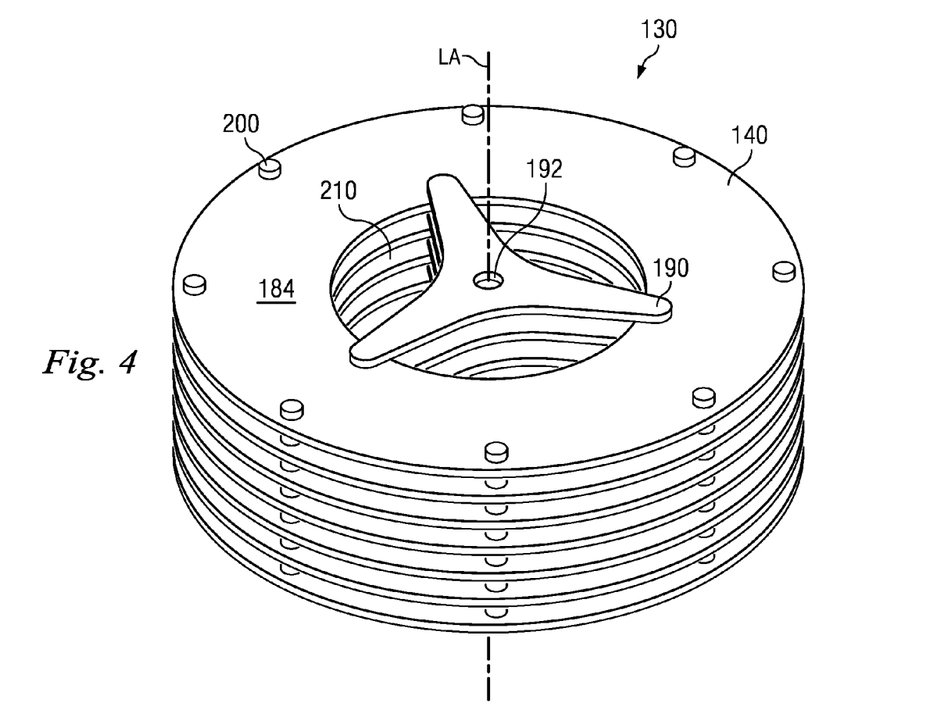
FIG. 4 is a perspective view of a portion of an ophthalmic instrument including a disk assembly according to an embodiment of the present disclosure.

FIG. 4 illustrates a perspective view of a disk assembly 130 according to an embodiment of the present disclosure. As shown in FIG. 4, the central aperture 180 of each of the disks 140 and the central opening 192 of each of the central spacers 190 are longitudinally aligned along the longitudinal axis LA of the pump 100 to form the disk assembly 130. The disk assembly 130 comprises the stacked array of alternating spacers 190 and disks 140 with distinct fluid flow passages 142 located between each disk 140. As described above, the inter-disk fluid flow passages 142 are maintained by the plurality of central spacers 190, which, together with the alternating disks 140, form a longitudinally aligned stack to create the disk assembly 130. In some embodiments, the drive shaft 134 extends longitudinally through the aligned and stacked central openings 192. The central apertures 180 of the disks 140 are aligned to form a central channel 210 extending longitudinally through the disk assembly 130. The central channel 210 is in fluid communication with the inlet port 106, and is preferably co-aligned with the inlet port 106. The central channel 210 is also in fluid communication with the fluid flow passages 142 and the space 144. The spacers 190 extend through the central channel 210 without unduly interrupting the flow of fluid axially and radially through the central channel 210.

As illustrated in FIG. 4, the connectors 200 function to maintain the disks 140 in a fixed relationship to one another, provide a physical aide in propelling the fluid out of the disk assembly 130, and help prevent the disks 140 from flexing or bending during operation of the pump 100. The connectors 200 are preferably aligned throughout the disk assembly 130. The connectors 200 extend from the face 184 of one disk 140 to the surface of an adjacent, more distally positioned disk to interconnect adjacent disks 140 via any of a variety of known methods, such as but not limited to, welding, adhesive, and magnetic or mechanical linkages.

The number of disks 140 in each disk assembly 130 may vary depending upon the particular application. In some embodiments, for example, the disk assembly 130 comprises between 2 and 20 disks. In general, for a specific pressure and volume of fluid, the larger the diameter of the disks employed in the disk assembly 130, the smaller the number of discs employed in the disk assembly 130, and visa-versa. In some embodiments, such as the embodiment pictured in FIG. 1, the pump 100 is housed in the handpiece of a surgical instrument, thereby allowing for an increased number of decreased size disks to pump a given volume of fluid at a specific pressure. In other embodiments, the pump 100 may be housed inside a console, thereby allowing for a decreased number of increased size disks to pump a given volume of fluid at a specific pressure.

Disk spacing (the height of the central spacers 190 and the fluid flow passages 142) must be sized to maximize the protective boundary layer effect (and thus efficiency), while at the same time being large enough to prevent occlusion or lodging of aspirated debris within the disk assembly 130. A stationary boundary layer separates the moving fluid from the facing surfaces of each disk 140. Therefore, the erosion or abrasion of the disks 140 is minimized even when the fluid contains abrasive or viscous matter. The thickness of the boundary layer is determined by the Reynolds number of the fluid being displaced. However, abrupt changes in the velocity and direction of the fluid can significantly reduce the thickness of the boundary layer. If the thickness of the boundary layer is reduced sufficiently, the abrasive particles in the fluid may abrade the surface of the disks 140 and the other components of the pump 100. The dimensions of the central spacers 190 (and therefore the height of the fluid flow passages 142) are variable and dependent upon the specific application of the pump 100 provided that debris and cellular material in the fluid are capable of passing through the fluid flow passages 142 without causing blockages in flow or abrading the disks 140. The height of the fluid flow passages 142 must be larger than the largest dimension of the particles in the fluid. For example, the spacing between each disk 150 (and therefore the height of the spacers 190) for ophthalmic applications may be in a range from 0.020 inches to 0.125 inches.

In alternative embodiments, the disk assembly may lack central spacers 190. In some embodiments, the pump may lack a drive shaft 134 and/or a central spacer 190. In such embodiments, the disks 140 may be connected to one another (and/or the proximal plate 150, and/or the distal plate 170) in a stable array of alternating disks 140 and fluid flow passages 142 by alternate known means such as, by way of example and not by way of limitation, rods extending through the faces 184.

In some embodiments, the entire disk assembly 130 may be constructed of plastics or other suitable material that may be shaped by any conventional method, such as injection molding or other comparable methods, to form an integrated disk assembly 130. An integrated disk assembly provides increased strength to the pump 100. In addition, an integrated disk assembly avoids various vibrational and mechanical wear problems associated with multi-piece disk assemblies. Additionally, an integrated disk assembly is more resistant to external forces than a multi-piece disk assembly. Alternatively, the individual components of the disk assembly 130 may be formed of a variety of known suitable materials, such as but not limited to, rigid plastics, metals, ceramics, and/or metal alloys.

Figure 5:
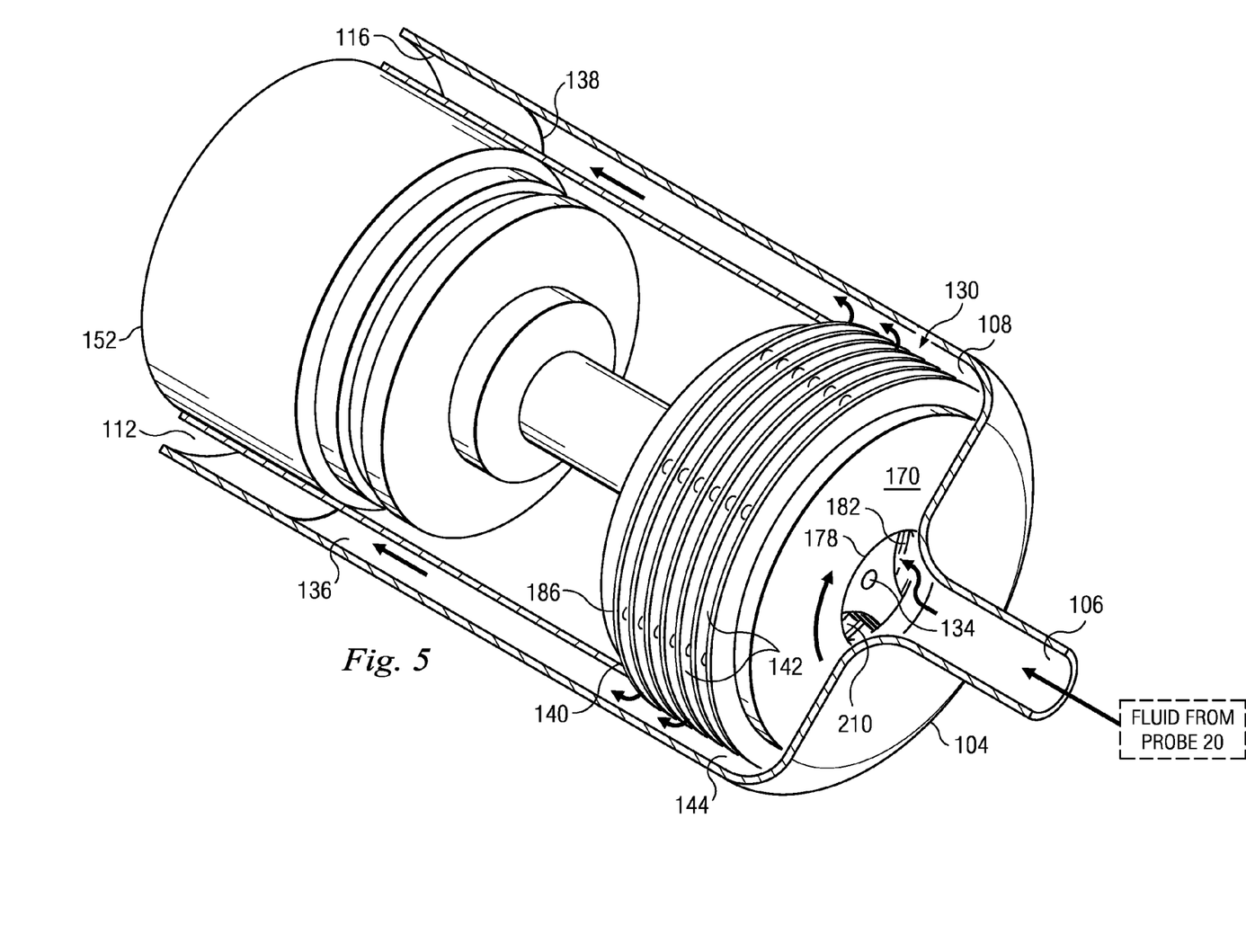
FIG. 5 is a perspective view of a portion of an ophthalmic instrument including a stacked multi-disk pump according to an embodiment of the present disclosure.

FIG. 5 illustrates the operation of the pump 100 within the ophthalmic instrument 10 pictured in FIG. 1. Initially, as shown in FIG. 1, the probe 20 is placed in fluid communication with the fluid to be pumped. For example, the distal end 40 of the probe may be positioned within an intraocular surgical site. Returning to FIG. 5, the fluid chamber 108 of the pump 100 is primed with a fluid compatible to the fluid to be pumped. The motor 152 is activated to impart rotational movement to the hub 154, which causes the simultaneous and identical rotation of the drive shaft 134 and the disk assembly 130. The fluid to be pumped travels through the probe 20 and enters the pump 100 through the inlet port 106. The fluid enters the fluid chamber 108 through a central aperture 178 in the distal plate 170 and flows into the central channel 210 of the disk assembly 130. As the disk assembly 130 rotates, the fluid is pulled into the fluid flow passages 142 between the plurality of disks 140. Most of the momentum transferred to the fluid is accomplished by rotation of the disks 140. As the disks 140 rotate through the fluid, the fluid in immediate contact with the disk 140 is also rotated due to the strong adhesion forces between the fluid and the disk 140.

Therefore, the rotation of the disk assembly 130 imparts momentum into the fluid in the fluid flow passages 142 sandwiched between the disks 140, thereby causing the fluid to move in the direction of the arrows. The viscous drag of the disks 140 allows momentum to be transferred from the disks to the rotating fluid. The viscous drag on the disks 140 exerts two forces on the fluid, one acting tangentially in the direction of rotation, and the other acting centrifugally in an outward radial direction (toward the inner wall 116 of the housing 104). Viscous drag results from the natural tendency of fluid to resist flow, and occurs whenever a velocity difference exists between a fluid and the container in which the fluid is located. The effect of viscous drag is to reduce the velocity difference between the fluid and the container. Therefore, as the disks 140 rotate, the fluid in the fluid flow passages 142 is also induced to move in the direction of rotation of the disks 140 and radially away from the central channel 210.

The combined effect of these forces propels the fluid with continuously increasing velocity in a spiral or helical flow path. Specifically, the drag on the fluid between the disks 140 induces circumferential and radial movement in the fluid, resulting in the fluid following a helical flow path radially outward into the annular space 144 located between the disk assembly 130 and the inner wall 116 of the housing. The momentum transfer begins slowly at the central channel 210 and increases as the fluid moves radially farther away from the central channel 210. The fluid eventually exits the disk assembly 140 from between the spaced disks 140, causing low pressure zones to form between the central channel 210 and the inside perimeter of the fluid flow passages 142 which encourages fluid to move radially outward from the central channel 210 and through the fluid flow passages 142, thus enabling a continuous flow process through the disk assembly 130. The continued movement of the accelerating fluid from the inside perimeter 182 of the disks 140 to the outside perimeter 186 of the disks 140 further draws fluid from the central channel 210, which is in fluid communication with the inlet port 106. The net negative pressure created within the central channel 210 of the disk assembly 130 draws more fluid from an outside source connected by any conventional means to the inlet port 106. Note that the pump 100 will not hold vacuum pressure if the motor 152 is not supplying rotational power to the disk assembly 130. Therefore, if the power fails or is turned off, the pump 100 will not hold vacuum pressure.

As the fluid is accelerated through the fluid flow channels 142 to the outside perimeter 186 of the disks 140, the continued momentum drives the fluid against the inner wall 116 of the housing 104, thereby creating a zone of higher pressure within the space 144 between the disk assembly 130 and the inner wall 116 of the housing 104. The fluid is driven from the zone of relative high pressure in the space 144 to a zone of relative low pressure defined by the outflow passage 136 and the outlet port 112. The fluid within the fluid chamber 108 may circulate a number of times before exiting the fluid chamber 108 through the outlet port 112. In this embodiment, the fluid outflow may be used to cool the motor 152 and/or the ophthalmic instrument 10 (shown in FIG. 1). In some embodiments having an inwardly angled shelf or groove in the inner wall 116, the shelf or groove serves to guide and aid the flow of circulating fluid toward the outlet port 112.

Figure 6:
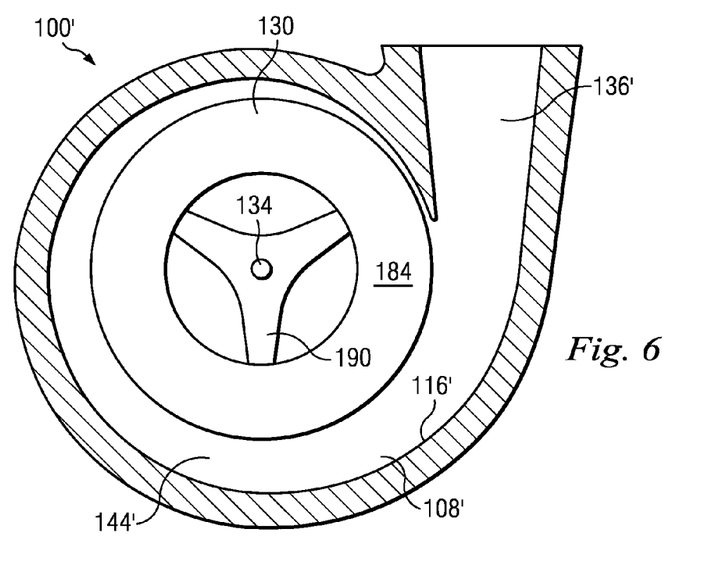
FIG. 6 is a cross-sectional plan view of a stacked multi-disk pump according to another embodiment of the present disclosure.

FIG. 6 illustrates a cross-sectional plan view of a pump 100' that is substantially similar to the pump 100 except for the differences to be described. The pump 100' includes an inner wall 116' configured such that a space 144' is not uniformly disposed around the disk assembly 130 and an outflow passage 136' is configured as a tube extending from a fluid chamber 108' to the outlet port 112. The inner wall 116' may be shaped and configured to create the gradually widening, generally annular space 144' around the disk assembly 130. The outflow passage 136' comprises a tube sized to have a diameter that may be generally the longitudinal length of the disk assembly 130. The space 144' is configured to direct the fluid radially into the outflow passage 136' and through the outflow valve 138. In the embodiment pictured in FIG. 6, the fluid follows a circumferential and radial path to exit the pump 100' without an abrupt change in the direction of flow.

The pressure and velocity at which the fluid is transported through the pump 100 is at least dependent upon the number of disks 140 in the disk assembly 130, the size of the fluid flow passages 142, the number, shape, size, and distribution of the connectors 200, the rotational speed of the disk assembly 130, the diameter of the disks 140, and the viscosity of the fluid being pumped. By varying the above factors, the pump 100 can be modified to pump a variety of fluids at a variety of desired pressures and flow rates. Moreover, the compact and bladeless design of a stacked multi-disk pump allows the system to be scaled down for placement within a handpiece or scaled up for placement in a console, for example, while maintaining relatively efficient performance and resistance to wear. Placement of the pump within a surgical handpiece allows the pump source to be positioned closer to the anterior chamber of the eye during an ophthalmic surgery, which may reduce the magnitude of a post-occlusion surge.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. An ophthalmic surgical instrument for pumping fluid from the eye of a patient, comprising:
   a cannulated probe; and
   a pump, comprising:
   a housing including a fluid chamber having a first portion and a second portion, an inlet port coupled to the probe, a motor housing chamber disposed within and separated from the second portion of the fluid chamber by a motor housing wall, and an outlet port;
   a disk assembly located within the first portion of the fluid chamber and comprising a stacked array of spaced apart parallel disks, each of the disks including a central aperture, wherein the disks are aligned and fixedly spaced from each other along a longitudinal axis extending through the central apertures; and
   a motor located within the motor housing chamber, the motor connected to the disk assembly and configured to rotate the disk assembly to convey fluid through the inlet port into the first portion of the fluid chamber, through the central apertures, between the spaced apart disks, through the second portion of the fluid chamber, and through the outlet port, wherein the second portion of the fluid chamber surrounds the motor housing chamber such that fluid flows between the motor housing wall and an inner wall of the fluid chamber to the outlet port.

2. The ophthalmic surgical instrument of claim 1, further comprising a handpiece, wherein the pump is disposed within the handpiece.

3. The ophthalmic surgical instrument of claim 1, further comprising a console separated from a handpiece, wherein the pump is disposed within the console.

4. The ophthalmic surgical instrument of claim 1, wherein the inlet port is configured to be positioned in direct fluid communication with fluid in the eye.

5. The ophthalmic surgical instrument of claim 1, wherein the fluid chamber is sized and configured to maintain a uniform, annular space between an outer periphery of the disk assembly and an inner wall of the housing.

6. The ophthalmic surgical instrument of claim 1, wherein the fluid chamber is sized and configured to create a nonuniform, annular space between an outer periphery of the disk assembly and an inner wall of the housing.

7. The ophthalmic surgical instrument of claim 1, wherein the disks of the disk assembly have gradually increasing diameters in a direction toward the outlet port.

8. The ophthalmic surgical instrument of claim 1, wherein the disks of the disk assembly have substantially equivalent diameters.

9. The ophthalmic surgical instrument of claim 1, further comprising a plurality of central spacers coupled to the disks and disposed within the disk assembly such that the disk assembly comprises an alternating array of disks and central spacers.

10. The ophthalmic surgical instrument of claim 9, wherein each of the central spacers comprise prongs fixedly attached to adjacent disks.

11. The ophthalmic surgical instrument of claim 9, wherein each of the central spacers is integrated into an adjacent disk.

12. The ophthalmic surgical instrument of claim 1, further comprising a plurality of connectors, the connectors comprising raised elements disposed on outer peripheries of the disks that interconnect adjacent disks and maintain the disks in a fixed relationship to one another.

13. The ophthalmic surgical instrument of claim 1, wherein the inlet port is interconnected with a proximal end of the probe by a snap-fit mechanism.

14. An ophthalmic surgical instrument for pumping fluid from an eye of a patient, comprising:
   a probe sized for insertion into the fluid in the eye; and
   a pump, comprising:

a housing including a fluid chamber, a motor housing chamber disposed within the fluid chamber, an inlet port, and an outlet port;

a hub located within the motor housing chamber;

a motor located within the motor housing chamber and connected to the hub such that the motor is configured to power rotation of the hub;

a drive shaft comprising an elongate, rigid rod connected to the hub such that rotation of the hub causes rotation of the drive shaft, the drive shaft extending through the fluid chamber along a longitudinal axis of the pump; and a disk assembly attached to the drive shaft and comprising a stack of parallel, circular disks, each disk extending radially and concentrically from the drive shaft and spaced axially apart from adjacent disks to form a plurality of fluid flow passages, each of the disks including a central aperture in fluid communication with the fluid flow passages, wherein the drive shaft extends through the central apertures, wherein rotation of the drive shaft causes rotation of the disk assembly to convey the fluid into the inlet port, through the central apertures and the fluid flow passages of the disk assembly, and through the outlet port.

15. The ophthalmic surgical instrument of claim 14, wherein the fluid chamber is sized and configured to maintain a uniform, annular space between an outer periphery of the disk assembly and an inner wall of the housing.

16. The ophthalmic surgical instrument of claim 14, wherein the disk assembly comprises an integrally-formed unit.

17. The ophthalmic surgical instrument of claim 14, wherein the disks of the disk assembly have gradually increasing diameters in a direction toward the outlet port.

18. The ophthalmic surgical instrument of claim 14, wherein the disks of the disk assembly have substantially equivalent diameters.

19. The ophthalmic surgical instrument of claim 14, further comprising a plurality of central spacers coupled to the disks and disposed within the disk assembly such that the disk assembly comprises an alternating array of disks and central spacers.

20. The ophthalmic surgical instrument of claim 14, further comprising a plurality of connectors, the connectors comprising raised elements disposed on outer peripheries of the disks that interconnect adjacent disks and maintain the disks in a fixed relationship to one another.

21. The ophthalmic surgical instrument of claim 14, further comprising an outflow valve comprising a one-way valve disposed between the disk assembly and the outlet port.

22. The ophthalmic surgical instrument of claim 14, further comprising an outflow passage comprising an annular space disposed circumferentially about the motor housing chamber.

* * * * *